(12) United States Patent
Lépine

(10) Patent No.: US 8,400,628 B2
(45) Date of Patent: Mar. 19, 2013

(54) ENCLOSURE FOR AN OPTICAL INSPECTION APPARATUS

(75) Inventor: Denis Lépine, Québec (CA)

(73) Assignee: Centre de Recherche Industrielle du Quebec, Quebec (CA)

( * ) Notice: Subject to any disclaimer, the term of this patent is extended or adjusted under 35 U.S.C. 154(b) by 35 days.

(21) Appl. No.: 13/184,024

(22) Filed: Jul. 15, 2011

(65) Prior Publication Data
US 2012/0274930 A1 Nov. 1, 2012

(30) Foreign Application Priority Data

Apr. 28, 2011 (CA) ..................................... 2738386

(51) Int. Cl.
*G01N 21/00* (2006.01)
*G01N 21/88* (2006.01)

(52) U.S. Cl. ................ 356/237.1; 356/237.2; 356/237.3

(58) Field of Classification Search .... 356/237.1–237.5, 356/601–623, 625, 629, 639, 640; 250/559.19, 250/559.21, 559.24, 559.25; 220/240, 244, 220/200; 271/3.16, 225
See application file for complete search history.

(56) References Cited

U.S. PATENT DOCUMENTS

| | | | |
|---|---|---|---|
| 4,202,612 A | | 5/1980 | Di Matteo et al. |
| 5,568,263 A | * | 10/1996 | Hanna ............................ 356/638 |
| 5,714,998 A | | 2/1998 | Wheeler |
| 5,761,070 A | | 6/1998 | Conners et al. |
| 5,960,104 A | | 9/1999 | Conners et al. |
| 6,046,764 A | | 4/2000 | Kirby et al. |
| 6,757,058 B1 | | 6/2004 | Carman et al. |
| 7,047,153 B2 | | 5/2006 | Woods et al. |
| 7,221,443 B2 | | 5/2007 | Akiyama |
| 7,227,165 B2 | | 6/2007 | Hubert et al. |
| 7,426,422 B2 | | 9/2008 | Carman et al. |
| 7,684,030 B2 | | 3/2010 | Berube et al. |
| 7,764,823 B1 | * | 7/2010 | Jurich et al. ................... 382/141 |
| 7,914,175 B2 | * | 3/2011 | Barker et al. ................. 362/259 |
| 2002/0025061 A1 | | 2/2002 | Metcalfe |

(Continued)

OTHER PUBLICATIONS

Schajer et al., Scanner System for Separate-Sided Lumber Surface Measurements Forest Products, Journal vol. 55, No. 12 Dec. 2005.

(Continued)

*Primary Examiner* — Sang Nguyen
(74) *Attorney, Agent, or Firm* — Jean-Claude Boudreau

(57) ABSTRACT

An enclosure for an optical inspection apparatus for scanning the profile of at least one surface of an article moving along a travel path axis, which apparatus having a frame for mounting a profile sensor unit using a laser source, includes a peripheral portion connected to the frame and forming spaced apart peripheral edges defining a space in which the frame and the profile sensor unit are contained, and front end and rear end portions each having an opening aligned with the travel path axis to allow the movement of the article through the apparatus. At least one of the front and rear end portions is provided with a pair of access doors having outer closing edges adapted to mate with corresponding portions of the peripheral edges, and inner closing edges adapted to mate one with another at first portions thereof, wherein at least one of the inner closing edges is provided with a clearance at a second portion thereof to define one of the openings whenever the access doors are brought one toward another to a closing position. The second portion is provided with at least one shielding element adjacent to the clearance to confine reflections of the laser beam within the enclosure while allowing the movement of the article.

6 Claims, 10 Drawing Sheets

U.S. PATENT DOCUMENTS

| | | | |
|---|---|---|---|
| 2004/0246473 | A1 | 12/2004 | Hermary et al. |
| 2006/0072111 | A1* | 4/2006 | Budd et al. .................... 356/427 |
| 2006/0109485 | A1* | 5/2006 | Laemmel ...................... 356/635 |
| 2007/0263918 | A1 | 11/2007 | Jenya |
| 2008/0029511 | A1 | 2/2008 | Barker et al. |
| 2010/0052237 | A1* | 3/2010 | Herczeg et al. .............. 271/3.16 |

OTHER PUBLICATIONS

Abbott et al., Automatic Scanning of Rough Hardwood Lumber for Edging and Trimming Proceedings of ScanTech 2001 International Conference Seattle (WA) USA. Nov. 4, 2001.

Kline et al. Lumber Scanning System for Surface Defect Detection 1992 International Winter Meeting ; American Society of Agricultural Engineers Nashville (TN) USA Dec. 15, 1992.

Kline et al. Evaluation of a Multi-Sensor Machine Vision System for Automated Hardwood Lumber Grading Proceedings: 4th International Conference on Image Processing and Scanning of Wood, IPSW Mountain Lake (VA) USA Aug. 21, 2000.

Lee et al. A Prototype Scanning System for Optimal Edging and Trimming of Rough Hardwood Lumber Proceedings of Scan Tech 2003 International Conference Seattle (WA) USA Nov. 4, 2003.

* cited by examiner

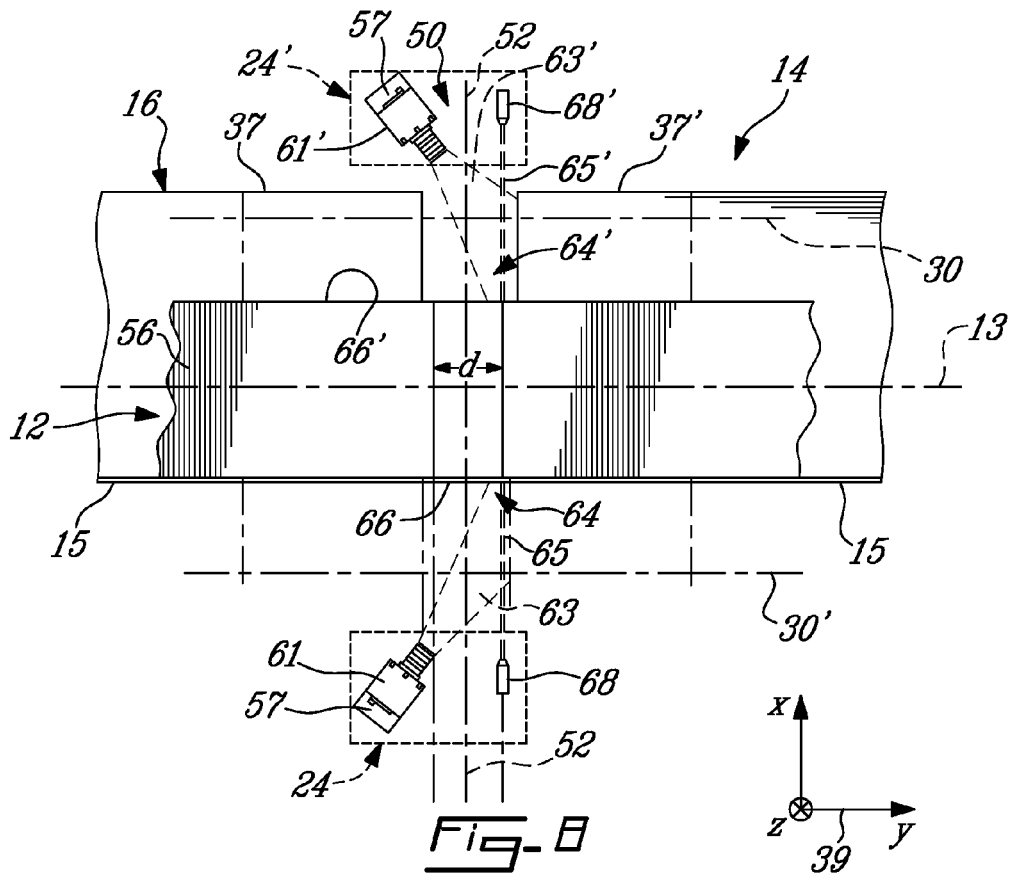
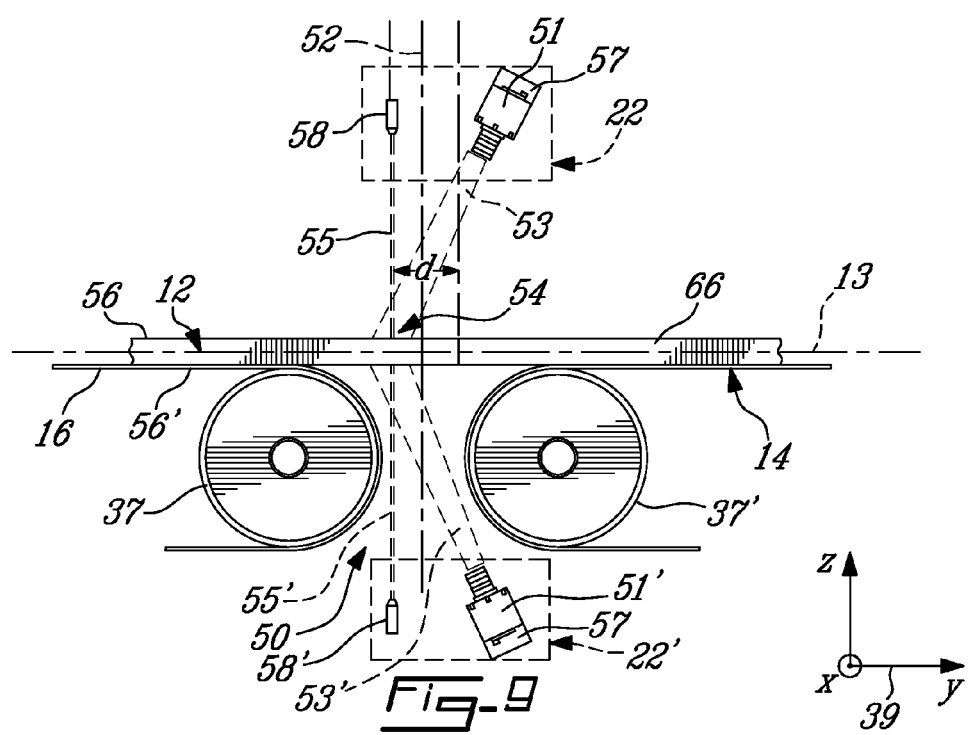

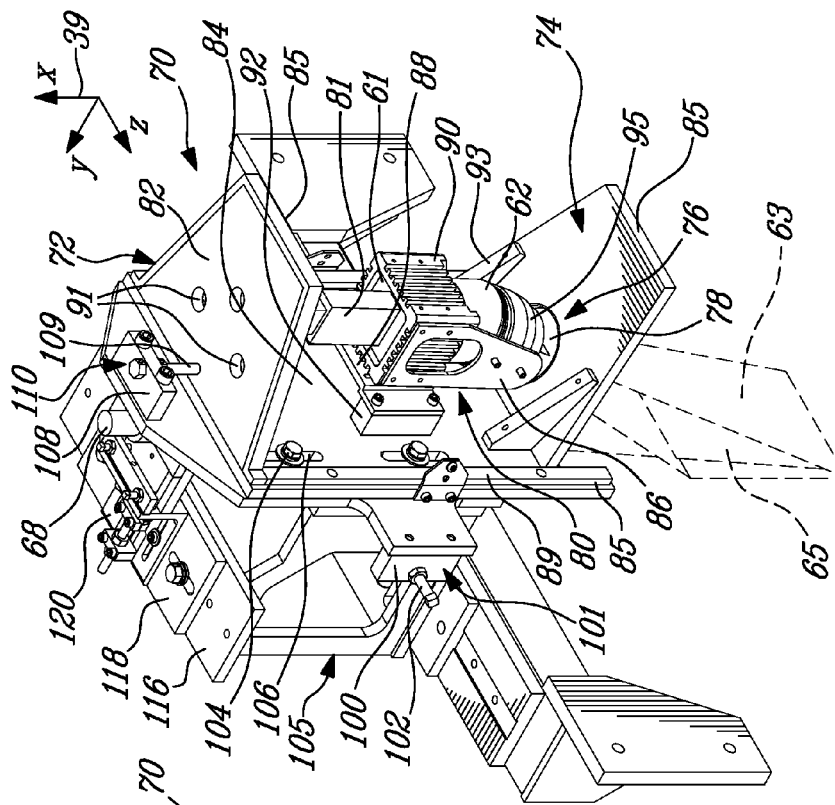
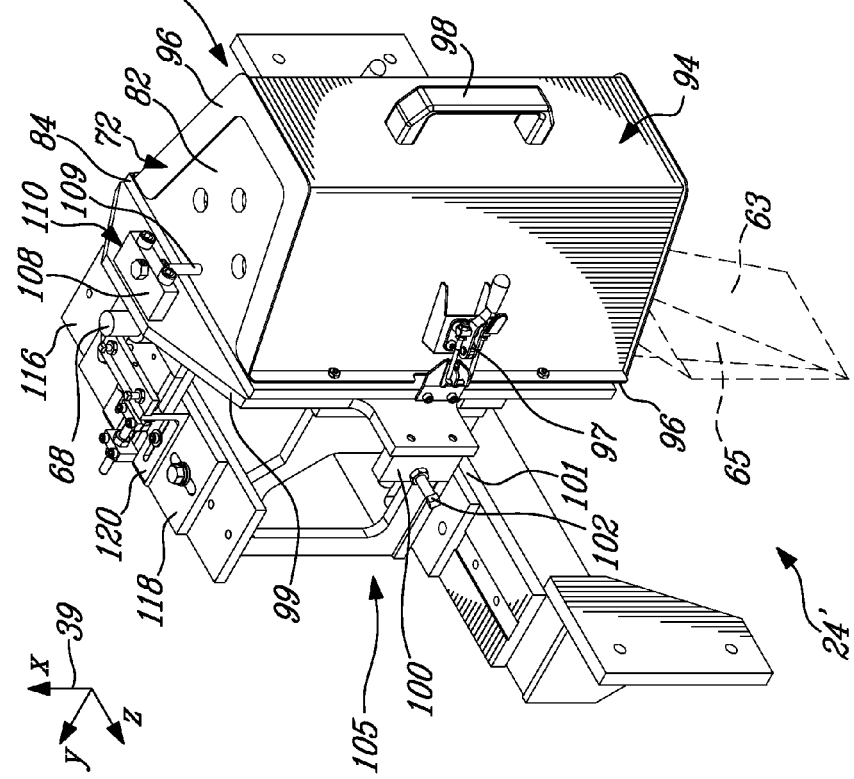

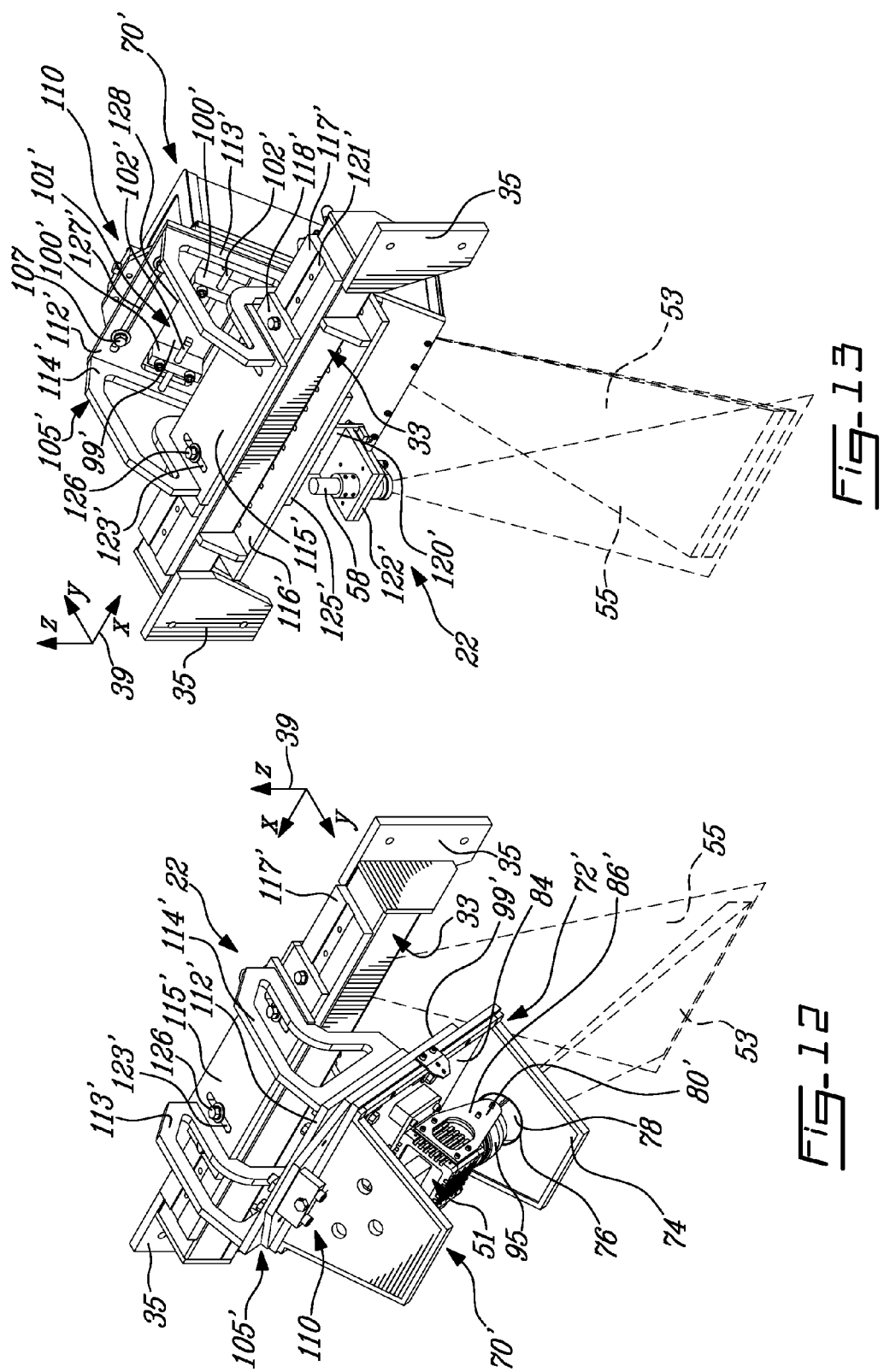

ENCLOSURE FOR AN OPTICAL INSPECTION APPARATUS

FIELD OF THE INVENTION

The present invention relates to the field of optical inspection technologies, and more particularly to enclosures for optical inspection apparatus using laser sources.

BACKGROUND OF THE INVENTION

During the past years, systems for scanning the surface of moving articles have been developed and applied for grading or quality control purposes in many high volume manufacturing applications such as found in the automotive, consumer electronics, agricultural, food or lumber processing industries. Such scanning systems typically use profile sensors based on laser triangulation to measure geometrical and other 3D surface characteristics of the inspected articles, which sensors makes use of digital cameras adapted to capture reflected light from a fan-shaped laser beam toward a scanning zone to define an associated scanning plane transverse to the travel path axis. It is known to provide and inspection system with a main enclosure for containing the profile sensors, such as disclosed in U.S. Pat. No. 7,684,030. A problem with known enclosures relates to the risk that reflected laser light leaks out through either entrance or exit of the inspection system and causes eye injury to plant operators.

SUMMARY OF THE INVENTION

There is a main object of the present invention to provide an enclosure for an optical inspection apparatus for scanning the profile of at least one surface of an article moving along a travel path axis, which enclosure confines within the enclosure reflections of a laser beam used by the apparatus while allowing the movement of the article therethrough.

According to the above mentioned object, from a broad aspect, there is provided an enclosure for an optical inspection apparatus for scanning the profile of at least one surface of an article moving along a travel path axis, the apparatus including a frame on which is mounted at least one profile sensor unit having a first optical sensing field directed toward the travel path axis and defining a first scanning zone associated with the surface as intersected by the sensing field, and a laser source directing at angle with the first sensing field a laser beam toward the scanning zone, to generate sensor output data related to the profile of the article surface. The enclosure comprises a peripheral portion connected to the frame and forming spaced apart peripheral edges defining a space in which the frame and the profile sensor unit are contained, and front end and rear end portions each having an opening aligned with the travel path axis to allow the movement of the article through the apparatus. At least one of the front and rear end portions is provided with a pair of access doors having outer closing edges adapted to mate with corresponding portions of the peripheral edges, and inner closing edges adapted to mate one with another at first portions thereof. At least one of the inner closing edges is provided with a clearance at a second portion thereof to define a corresponding one of the openings whenever the access doors are brought one toward another to a closing position. The second portion is provided with at least one shielding element adjacent to the clearance to confine reflections of the laser beam within the enclosure while allowing the movement of the article.

BRIEF DESCRIPTION OF THE DRAWINGS

Preferred embodiments of the present invention will now be described in detail with reference to the accompanying drawings in which:

FIG. 2A is a detailed view of the entrance opening provided on the apparatus enclosure of FIG. 2, showing the shielding element provided to confine reflections of said laser beam within the apparatus enclosure;

FIG. 8 is a schematic sectional view of the apparatus along section lines 8-8 of FIG. 6, illustrating the configuration of optical elements used for scanning the article side surfaces;

FIG. 9 is a schematic sectional view of the apparatus along section lines 9-9 of FIG. 6, illustrating the configuration of optical elements used for scanning the article top and bottom surfaces;

FIGS. 10 and 10A are perspective front views of a first example of profile sensor unit provided on the apparatus of FIG. 6, showing the camera enclosure with a mounting assembly of a first design, respectively illustrated with the enclosure cover, and without the enclosure cover to show a camera at its mounting location;

FIG. 12 is a perspective front view of a second example of profile sensor unit provided on the apparatus of FIG. 6, showing the camera enclosure with a mounting assembly of a second design; and FIG. 13 is a perspective rear view of the profile sensor unit of FIG. 12.

DETAILED DESCRIPTION OF THE PREFERRED EMBODIMENTS

Figure 1:
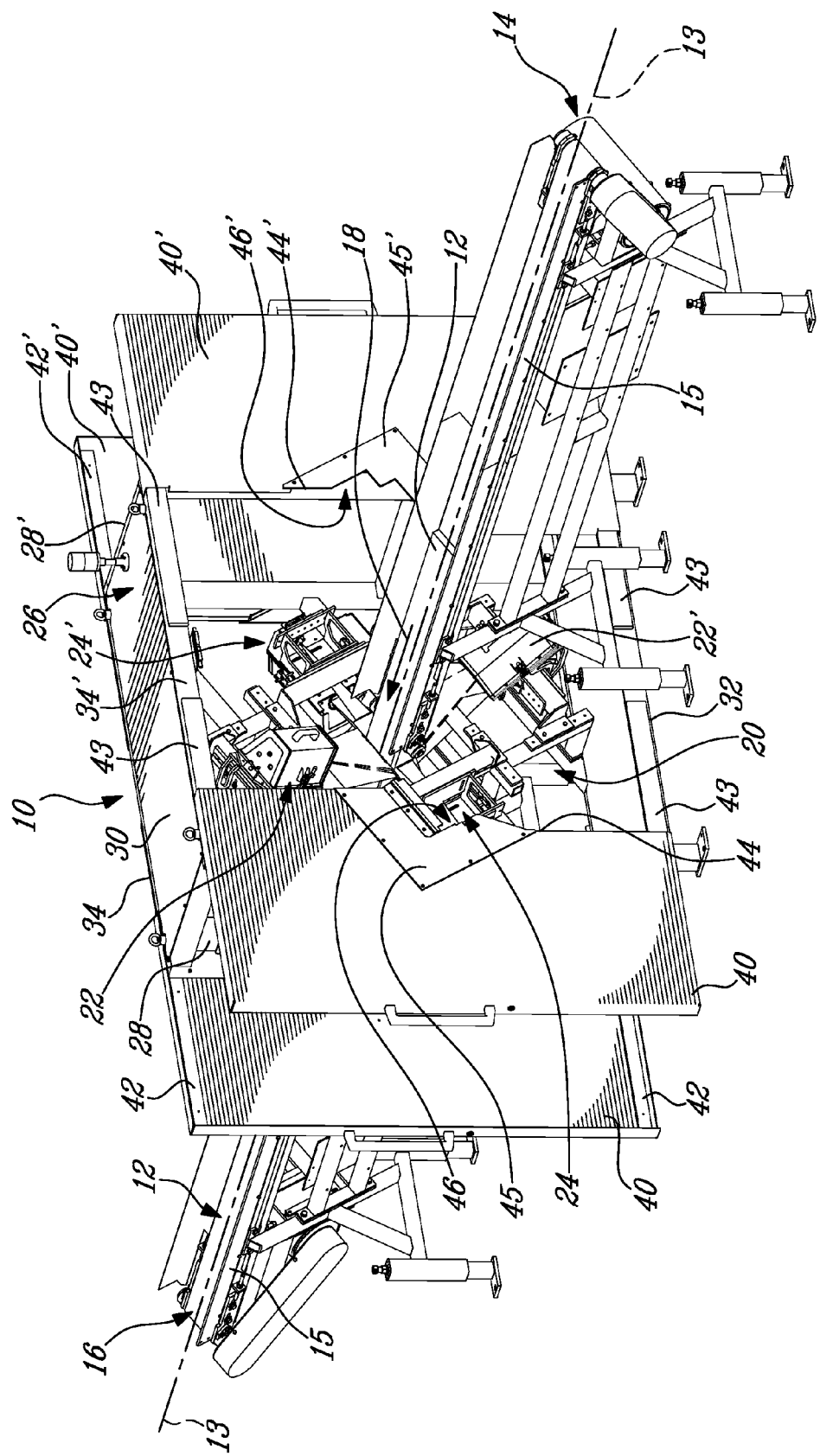
FIG. 1 is a perspective view of an example of inspection apparatus designed for simultaneously scanning the profile of four adjacent surfaces of an article, which has infeed and outfeed conveyer units for moving the article to be inspected through the apparatus, showing front access doors provided on the apparatus enclosure in their open positions.

Referring now to FIG. 1, there is shown an example of inspection apparatus as generally designated at 10, which is designed for simultaneously scanning the profile of four adjacent surfaces of an article 12, which is a wooden board to be inspected in the present example. It is to be understood that the optical inspection apparatus and method as described below may be used to inspect articles of any nature, material or shape. The profile data can be used to detect profile-related board characteristics including geometrical and surface defects such as wane, holes, knots, cracks etc., using known detection techniques such as disclosed in prior U.S. published Patent application no. 2010/0188500 and U.S. Pat. No. 6,122, 065 naming the same assignee as of the present invention. The detected characteristics are typically fed to a cut optimizer software providing a cutting solution into subdivided products from each board, producing an optimum yield in term of either economic value or material utilization. Any appropriate optimization approach can be used, including a one-axis or two-axis optimization approach such as described in U.S. Pat. No. 6,690,990 issued to the same assignee as of the present invention. For example, the exemplary system 10 may be used by a furniture or floorwood manufacturing plant to increase production yields by upgrading wood products in view of raw wooden board quality and by minimizing the impact of any raw wood quality decrease upon profitability and performance of the manufacturing plant.

Figure 6:
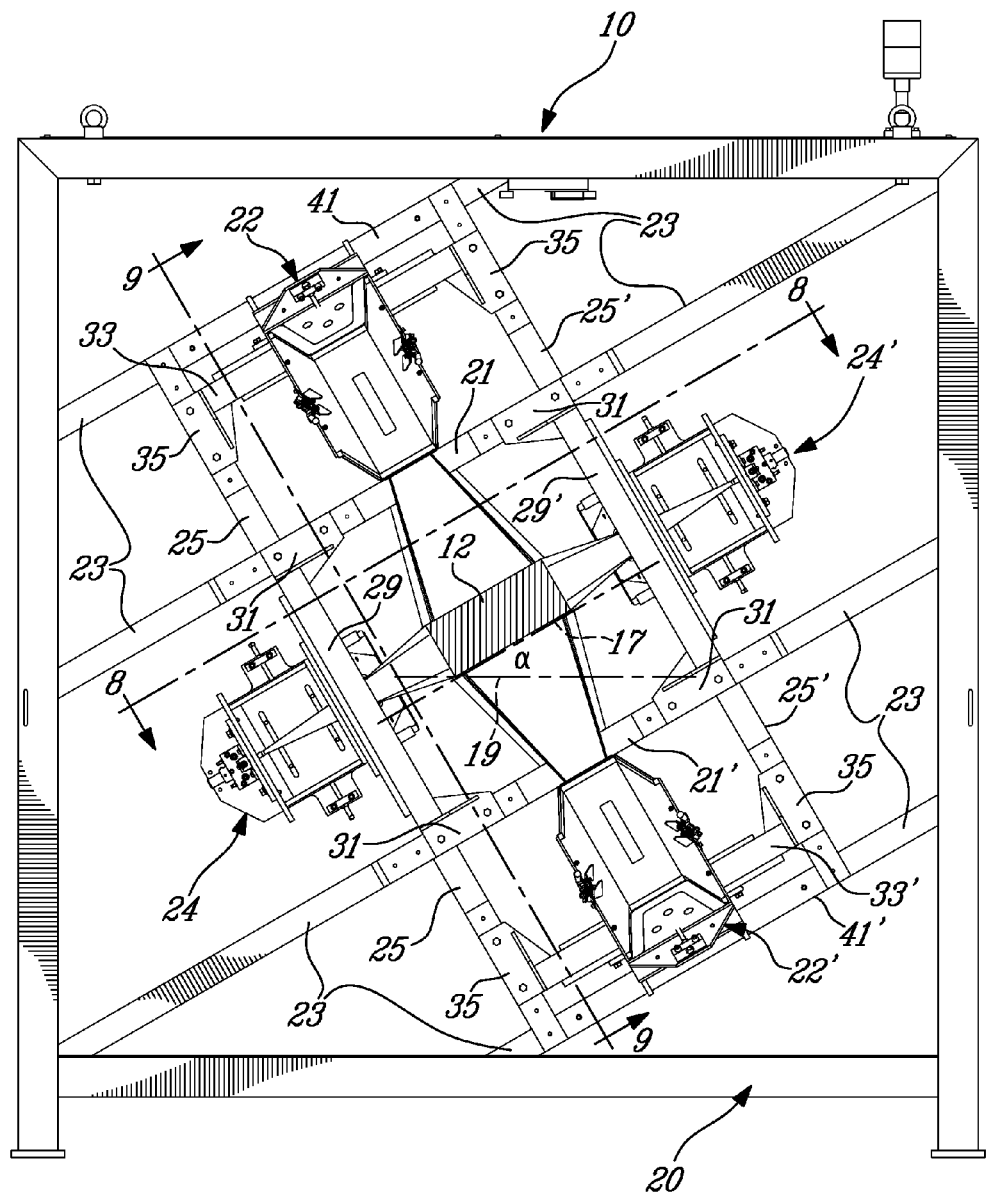
FIG. 6 is a front view of the apparatus of FIG. 1 with its access doors and conveyer units not illustrated to better show the internal optical and mechanical components of the apparatus.

As shown on FIG. 1 in view of FIG. 6, the apparatus 10 has an infeed conveyer unit 14 and an outfeed conveyer unit 16 for moving the board 12 to be inspected through the apparatus along a travel path axis 13 in the direction of arrow 18. In the present embodiment, the transporting plane of each conveyer unit 14,16, which is designated at 17 on FIG. 6, is preferably at an angle α of about 30° with respect to a horizontal plane designated at 19 so that a fed board 12 is caused to urge under gravity against a guide 15 provided on each conveyer unit 14,16. However, conveyers for transporting boards according to another orientation such as parallel to the horizontal plane, could also be used, by providing appropriate adaptation. The apparatus 10 is particularly adapted to receive wooden boards from wood processing equipment capable of machining top, bottom and both side surfaces of each board, for inspection thereof. The apparatus 10 is provided with a frame 20 on which are mounted laser-based, profile sensor units 22, 22' and 24, 24', using pairs of cross-bars 25, 25' and a further pair of cross-bars 21, 21', which cross-bars are secured to frame bars 23 through members 27 shown on FIG. 7. The profile sensor units 24, 24' are adjustably held on cross-bars 21, 21' using support members 29, 29', bolted at both ends 31 thereof. Conveniently, the profile sensor units 22, 22' are adjustably held on respective pairs of cross-bars 25, 25' using support members 33, 33' bolted at both ends 35 thereof. Further cross-bars 41, 41', are provided to strengthen the mounting arrangement. It is to be understood that any other configuration of mounting arrangement can be used to adjustably secure the profile sensor units onto the apparatus frame 20.

Referring again to FIG. 1, the apparatus 10 is protected and isolated from its working environment by an enclosure 26 having a peripheral portion formed by side walls 28, 28' top wall 30 and bottom wall 32 connected to the frame 20 and forming spaced apart front and rear peripheral edges 34, 34' defining a space in which the frame 20 and the profile sensor units 22, 22' and 24, 24' are contained. As shown on FIG. 2 in view of FIG. 1, the apparatus enclosure 26 includes front end and rear end portions 36, 36' each having an opening 38 aligned with the travel path axis 13 to allow the movement of board 12 through the apparatus 10. At least one of front and rear end portions 36, 36' is provided with a pair of access doors 40, 40' having outer closing edges 42, 42' adapted to mate with corresponding portions of the peripheral edges 34, 34', and inner closing edges 44, 44' adapted to mate one with another at first portions thereof, which, in the example shown, are located on the upper and lower parts of the doors 40, 40' and partially extend along opening plates 45, 45' provided thereon, as better shown on FIG. 2A. As shown on FIG. 1, the peripheral edges 34 and 34' are conveniently provided at their respective upper and lower portions with holding rails 43 designed to engage corresponding upper and lower portions of the outer closing edges 42, 42' to allow sliding of access doors 40, 40' which are provided with bearings. It is to be understood that any other appropriate access door type, such as using hinges located on lateral portions of the peripheral edges 34, 34', could alternatively be used. At second portions of inner closing edges 44, 44', there are provided clearances 46, 46' to define the corresponding opening 38 shown on FIG. 2A, whenever the access doors 40, 40' are brought one toward another from an open position as shown on FIG. 1 to a closing position as shown on FIG. 2. Conveniently, the second portions of inner closing edges 44, 44' defining the opening 38 are part of opening plates 45, 45', respectively.

For safety purposes, to minimize the risk that any reflected laser light leaks out through apparatus opening 38 and causes eye injury to plant operators, as better shown on FIG. 2A, adjacent the clearance portion 46, the second portion of inner closing edges 44 as part of opening plate 45 is provided with a shielding element 48 attached to a holder 49 to confine reflections of the laser beams produced by the profile sensor units 22, 22' and 24, 24', within the enclosure while allowing the movement of the board 12. The shielding element 48 may be made of any appropriate material, and preferably of a flexible material such as plastic, rubber or fabric, in any appropriate form such as a strip, curtain or brush, as a unitary piece or constituted of a plurality of elements such as fibres, provided it is sufficiently opaque to laser light. Optionally, for providing adaptation to various board dimension values (thickness in the example shown), the shielding element 48 may be rendered adjustable with respect to the closing edges 44 by providing the holder 49 with an appropriate mechanism, especially in a case where the material of which the shielding element is made is rigid, to minimize gaps through which reflected laser light may leak out, while ensuring unrestricted passage of boards through the apparatus.

Figure 2:
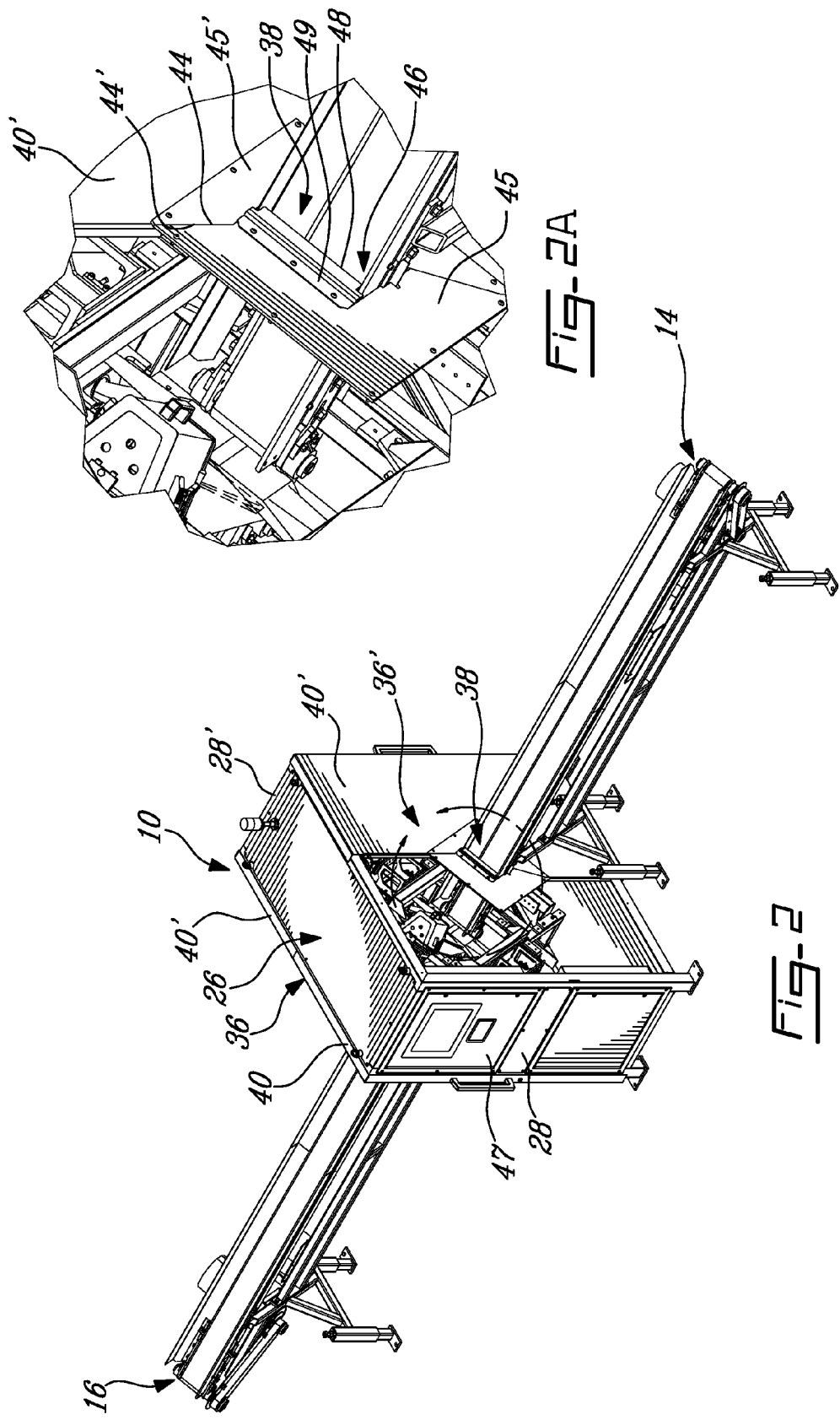
FIG. 2 is a perspective view of the inspection apparatus of FIG. 1, showing front access doors in their closed positions and without the inspected article, the left one being partially cut away to show the infeed conveyer unit extending within the apparatus enclosure behind the exit opening.
Figure 3:
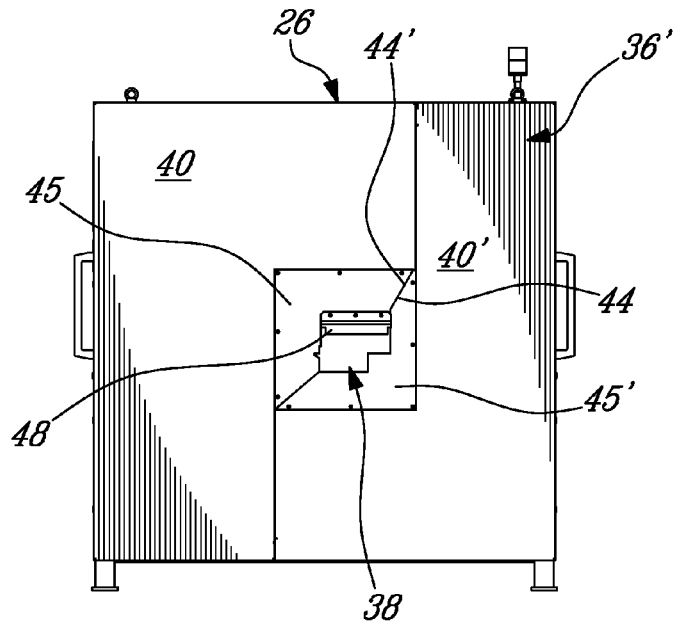
FIGS. 3 to 5 are end views of apparatus enclosures showing various designs of entrance/exit openings.
Figure 4:
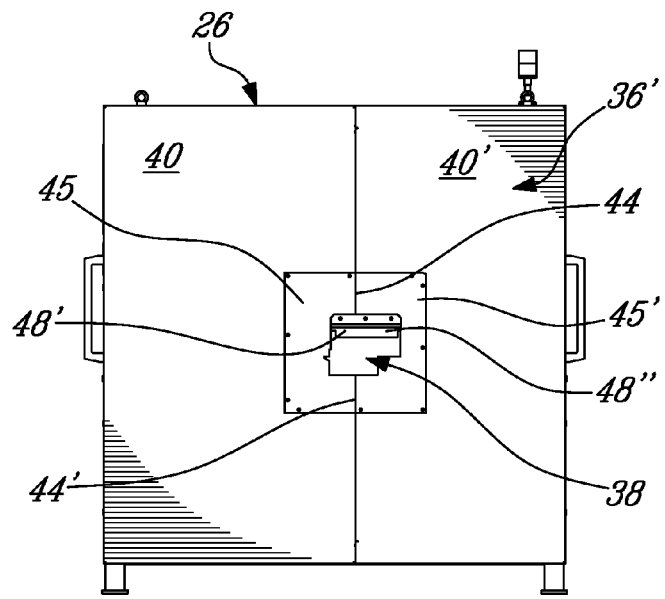
Figure 5:
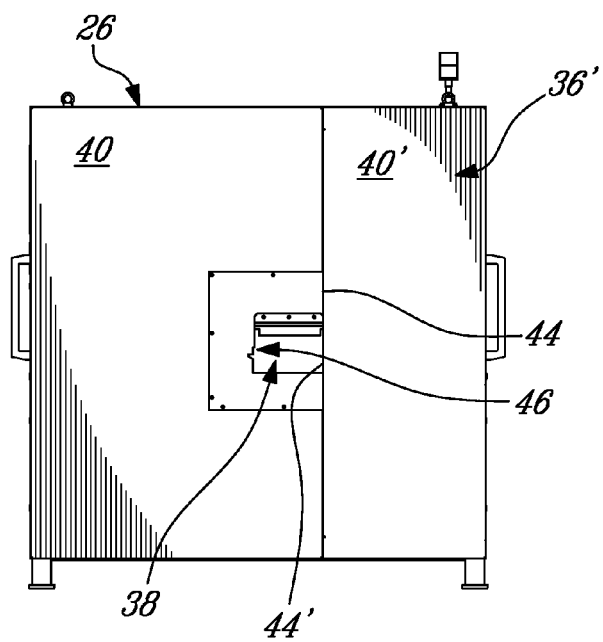

Referring now to FIGS. 3 to 5, there are shown apparatus enclosures showing various designs of opening that could be used either as exit opening 38 at rear end portion 36' of enclosure 26 as illustrated, or as entrance opening (not shown) at front end portion 36. On FIG. 3, there is shown a design of opening plates 45, 45' provided on left and right doors 40, 40', which are adapted to receive therethrough infeed and outfeed conveyer units installed in a horizontal orientation. As for the embodiment described before in view of FIGS. 1 to 2A, the opening plate 45 forming the second portions of inner closing edges 44 is provided with a shielding element 48 to confine reflections of the laser beams produced by the profile sensor units within the enclosure whenever the access doors 40, 40' are brought one toward another to their respective closing positions. Turning now to FIG. 4, there is shown another design of opening plates 45, 45' adapted to horizontal conveyer units, wherein the inner closing edges 44, 44' extend along a straight line separating the opening 38 in two parts, a left one being defined by opening plate 45, while a right one is defined by opening plate 45'. In this case, the second portion of each inner closing edge 44, 44' is provided with its own shielding element 48', 48" to confine reflections of the laser beams produced by the profile sensor units within the enclosure whenever the access doors 40, 40' are brought one toward another to their respective closing positions. Turning now to FIG. 5, there is shown another design adapted to horizontal conveyer units, wherein only the inner closing edge 44 is provided with a clearance 46 to define the opening 38. In that case, a single opening plate 45 can be provided on access door 40 at second portion of inner closing edge 44 thereof, while the second portion of inner closing edge 44' provided on access door 40' extends along a straight line to complete delimitation of clearance 46. Here again, the opening plate 45 forming the second portion of inner closing edge 44 is provided with a single shielding element 48 to confine reflections of the laser beams produced by the profile sensor units within the enclosure whenever the access doors 40, 40' are brought one toward another to their respective closing positions.

A particular compact arrangement of the profile sensor units as part of the apparatus 10 will now be described in detail with reference to the schematic sectional views of FIGS. 8 and 9. It can be seen that the conveyer units 14 and 16 are respectively provided with conveyer rolls 37, 37' which define, in the example shown, the limits of an inspection area 50 located at a central plane designated at 52 which is transverse to the travel path axis 13, and equidistant to the conveyer rolls 27 and 27'. It can be appreciated that the spacing between conveyer rolls 27 and 27' determines the minimum length a board 12 must have in order to be longitudinally transported through the inspection apparatus. Therefore, in order to accept a wide range of board lengths (in direction of Y axis on the reference system 39), the conveyer rolls spacing has to be minimized, while leaving the optical clearance required by the scanning of board of various widths (in direction of X axis on the reference system 39). The width of the transporting surface of the conveyer units 14 and 16, starting from the guide 15, is made sufficient to provide board feeding adaptation to boards of various width values, up to the largest board width limit indicated in dotted lines 30 adjacent profile sensor unit 24' also represented in dotted lines on FIG. 8. It is to be understood that in any case where the conveyers for transporting the boards 12 are designed to work without a guide 15 extending within the adjacent to the inspection area 50, for example according to another orientation such as parallel to the horizontal plane, the conveyer width may extend on the other side of the travel path axis 13 toward profile sensor unit 24, up to a further board width limit as indicated by dotted line 30'.

It can be seen from FIG. 9 that the first profile sensor unit 22 represented in dotted lines includes a first digital camera 51 having a first optical sensing field 53 directed toward the travel path axis 13 and defining a first scanning zone 54 associated with a first board surface 56 (top surface in the example shown) as intersected by the first sensing field 53. A digital 3D camera such as model C3-2350 from Automation Technology Gmbh (Germany) may be used. The first profile sensor unit 22 also includes a first laser source 58 directing at angle with the first sensing field 53 a first fan-shaped laser beam 55 toward the first scanning zone 54 to define an associated first scanning plane transverse (within plane X-Z in reference system 39) to the travel path axis 13. A laser such as model SNF-701L-660S-100-30 from Coherent Inc. (Santa Clara, Calif.) may be used, with transverse fan angle of about 30°. It is to be understood that any other appropriate laser available in the marketplace can be used. The first profile sensor unit is provided with a data processing module 57 to generate output data related to the profile of the first board surface 56 through triangulation ranging, which profile is associated with a reference axis (axis Z in reference system 39) orthogonal to a reference plane (plane X-Y in reference system 39) parallel to the travel path axis. For so doing, the digital camera 51 captures a two-dimensional image of a first reflected laser line formed by the laser beam onto the first surface 56 to generate corresponding first two-dimensional image data, from which the data processing module 57 derives the profile-related output, involving calculation of the center of gravity of the laser beam image, or any other appropriate algorithm. The profile sensor unit may conveniently use a same laser triangulation ranging approach as disclosed in U.S. Pat. No. 7,429,999 issued to same assignee as of the present invention. The processing module can be wholly or partially integrated into the camera 51, or be part of a computer system interfaced with the camera to receive and process two-dimensional image data therefrom, which computer may be provided in a control panel 47 as shown in FIG. 2.

Turning back to FIG. 8, there is shown a second profile sensor unit 24 represented in dotted lines including a second digital camera 61 having a second optical sensing field 63 directed toward the travel path axis 13 and defining a second scanning zone 64 associated with a second board surface 66 (left side in the example shown) adjacent to first (top) board surface 56, the second scanning zone 64 being intersected by the second sensing field 63. A digital 3D camera such as model C3-2350 from Automation Technology Gmbh (Germany) may also be used preferably provided with a "Scheimpflug" adapter to amplify the optical depth of field of the profile sensor unit 24 to provide inspection capability of the apparatus to boards of various widths, as will be described later in more detail. The second profile sensor unit 24 also includes a second laser source 68 directing at angle with the second sensing field 63 a second fan-shaped laser beam 65 toward the second scanning zone 64 to define an associated second scanning plane transverse (within plane X-Z in reference system 39) to the travel path axis 13. A same laser model such as provided on the first profile sensor unit 22 may be used, with transverse fan angle of about 10°. The second profile sensor unit 24 is also provided with a data processing module 57 to generate output data related to the profile of the second board surface 66 through same triangulation ranging approach employed by the first profile sensor unit 22, which profile is in this case associated with a reference axis (axis X in reference system 39) orthogonal to a reference plane (plane Z-Y in reference system 39) parallel to the travel path axis 13. For so doing, the digital camera 61 captures a two-dimensional image of a second reflected laser line formed by the laser beam 65 onto the second surface 66 to generate corresponding second two-dimensional image data, from which the data processing module 57 derives the profile-related output. Here again, the processing module can be wholly or partially integrated into the camera 61, or be part of a computer system interfaced with the camera to receive and process two-dimensional image data therefrom.

Referring again to FIG. 9 in view of FIG. 8, it can be appreciated that the first and second profile sensor units 22, 24 are disposed one with respect to another so that their respective first and second scanning zones 54, 64 are sufficiently spaced one with another along the travel path axis 13 to substantially prevent mutual scanning interference between first and second profile sensors. In the example shown, since first (top) and second (left side) surfaces are adjacent one with another, the first scanning plane associated with the first laser beam 55 and the second scanning plane associated with the second laser beam 65 are offset by a distance "d" in order to prevent illumination interference that would otherwise be caused by laser beam 55 in scanning zone 54 on cameras 61 of profile sensor unit 24, and reciprocally by laser beam 65 in scanning zone 64 on cameras 51 of profile sensor unit 22. It can be appreciated that although simultaneous scanning of the profile of the adjacent surfaces 56, 66 may be carried out, the first and second scanning planes being non coplanar due to the offset distance "d", the scanned areas on adjacent surfaces are consequently not coplanar with respect to the reference axis (axis Y on the reference system 39) parallel to the travel path axis 13. Therefore, there is a need for assembling respective output data generated by profile sensor units 22, with corresponding data representing location along that reference axis. A method for that purpose is described in U.S. published application no. 2010/0189135 naming the same assignee as for the present invention. It is to be understood that any other appropriate data assembling technique can be used.

Furthermore, to provide a compact arrangement of first and second profile sensor units 22 and 24, it can also be appreciated in the example illustrated on FIGS. 8 and 9, that the first sensing field 53 is crossing the central plane 52 toward the first laser beam 55, whereas the second sensing field 63 is crossing the central plane 52 toward the second laser beam 65. According to the profile sensor configuration shown on FIGS. 8 and 9, the first laser beam 55 is directed toward the first scanning zone 54 within the first scanning plane, and similarly, the second laser beam 65 is directed toward the second scanning zone 64 within the second scanning plane. This configuration allows to minimize the conveyer rolls spacing at a value near offset distance "d" while providing the optical clearance required by the scanning of boards within the desired ranges of board widths and lengths. In the example shown, the first (top) surface 56 is a main surface associated with a first dimension (width) transverse to the travel path axis 13 and of a value selected from a first range of dimension values. The second surface 66 is a side (left) surface associated with a second dimension (thickness) transverse to the travel path axis 13 and of a value selected from a second range of dimension values. According to the proposed compact configuration, the first optical sensing field 53 has a depth adapted to define the first scanning zone 54 for any selected value of second dimension (thickness), whereas the second optical sensing field 63 has a depth adapted to define the second scanning zone 64 for any selected value of first dimension (width).

According to an alternate configuration of profile sensor units (not shown), the first sensing field 53 may be directed toward the travel path axis 13 within the first scanning plane (along Z axis of reference system 39), and similarly, the second sensing field 63 may be directed toward the travel path axis 13 within the second scanning plane. In that case, a similar compact arrangement can be obtained if the first laser beam 55 is crossing the central plane toward the first sensing field 53, whereas the second laser beam 65 is crossing the central plane toward the second sensing field 63.

While the proposed inspection apparatus may be basically used to scan two adjacent surfaces of an board by means of profile sensor units 22 and 24, as mentioned above, the embodiment shown on FIGS. 1-2A and 6-9 is designed for simultaneously scanning the profile of four adjacent surfaces of an article, such as a wooden board also having a bottom surface 56' and a second side surface 66' (right side in the example shown) adjacent thereto. For so doing, third and fourth profile sensor units 22' and 24' are provided according to a symmetrical configuration as compared to that which involves profile units 22 and 24 as described above.

Referring again to FIG. 9, the third profile sensor unit 22' represented in dotted lines includes a third digital camera 51' having a third optical sensing field 53' directed toward the travel path axis 13 and defining a third scanning zone 54' associated with the third board surface 56' (bottom surface in the example shown) as intersected by the third sensing field 53'. A same digital 3D camera such as the one provided on profile sensor unit 22 may be used. The third profile sensor unit 22' also includes a third laser source 58' directing at angle with the third sensing field 53' a third fan-shaped laser beam 55' toward the third scanning zone 54' to define an associated third scanning plane transverse (within plane X-Z in reference system 39) to the travel path axis 13. A same laser such as the one provided on first profile sensor unit 22 may be used. The third profile sensor unit is provided with a data processing module 57 to generate output data related to the profile of the third board surface 56' through triangulation ranging, which profile is associated with a reference axis (axis Z in reference system 39) orthogonal to a reference plane (plane X-Y in reference system 39) parallel to the travel path axis 13. For so doing, the digital camera 51' captures a two-dimensional image of a third reflected laser line formed by the laser beam onto the third surface 56' to generate corresponding third two-dimensional image data, from which the data processing module 57 derives the profile-related output, involving calculation of the center of gravity of the laser beam image, or any other appropriate algorithm, with the same laser triangulation ranging approach as mentioned above.

Turning back to FIG. 8, the fourth profile sensor unit 24' is shown, which includes a fourth digital camera 61' having a fourth optical sensing field 63' directed toward the travel path axis 13 and defining a fourth scanning zone 64' associated with a fourth board surface 66' (right side in the example shown) adjacent to third (bottom) board surface 56', the fourth scanning zone 64' being intersected by the fourth sensing field 63'. A same digital 3D camera such as provided on the second profile sensor unit 24 may be used. The fourth profile sensor unit 24' also includes a fourth laser source 68' directing at angle with the fourth sensing field 63' a fourth fan-shaped laser beam 65' toward the fourth scanning zone 64' to define an associated fourth scanning plane transverse (within plane X-Z in reference system 39) to the travel path axis 13. A same laser model such as provided on first profile sensor unit 22 may be used. The fourth profile sensor unit 24' is also provided with a data processing module 57 to generate output data related to the profile of the fourth board surface 66' through same triangulation ranging approach employed by the first profile sensor unit 22, which profile is in this case associated with a reference axis (axis X in reference system 39) orthogonal to a reference plane (plane Z-Y in reference system 39) parallel to the travel path axis 13. For so doing, the digital camera 61' captures a two-dimensional image of a fourth reflected laser line formed by the laser beam 65' onto the second surface 66' to generate corresponding fourth two-dimensional image data, from which the data processing module 57 derives the profile-related output.

Referring again to FIG. 9 in view of FIG. 8, it can be appreciated that the third and fourth profile sensor units 22', 24' are also disposed one with respect to another so that their respective third and fourth scanning zones 54', 64' are sufficiently spaced one with another along the travel path axis 13 to substantially prevent mutual scanning interference between third and fourth profile sensors.

In the example shown, since third (bottom) and fourth (right side) surfaces are adjacent one with another, the third scanning plane associated with the third laser beam 53' and the fourth scanning plane associated with the fourth laser beam 63' also offset by a distance "d" in order to prevent illumination interference that would otherwise be caused by laser beam 55' in scanning zone 54' on camera 61' of profile sensor unit 24' (as well as on camera 61 of profile sensor unit 24), and reciprocally by laser beam 65' in scanning zone 64' on cameras 51' of profile sensor unit 22' (as well as on camera 51 of profile sensor unit 22). Furthermore, to provide a similar compact arrangement as obtained with the first and second profile sensor units 22 and 24 described above, it can also be appreciated in the example illustrated on FIGS. 8 and 9, that the third sensing field 53' of profile sensor unit 22' is crossing the central plane 52 toward the third laser beam 55', whereas the fourth sensing field 63' is crossing the central plane 52 toward the fourth laser beam 65'. According to the profile sensor configuration shown on FIGS. 8 and 9, the third laser beam 55' is directed toward the third scanning zone 54' within the third scanning plane, and similarly, the fourth laser beam 65' is directed toward the fourth scanning zone 64' within the fourth scanning plane. Here again, this configuration allows to minimize the conveyer rolls spacing at a value near offset distance "d" while providing the optical clearance required by the scanning of boards within the desired ranges of board widths and lengths. In the example shown, the third (bottom) surface 56' is a main surface associated with the same first dimension (width) transverse to the travel path axis 13 and of a value selected from the first range of dimension values. The fourth surface 66' is the other side (right) surface associated with the same second dimension (thickness) transverse to the travel path axis 13 and of a value selected from the second range of dimension values. Here again, according to the proposed compact configuration, the third optical sensing field 53' has a depth adapted to define the third scanning zone 54' for any selected value of second dimension (thickness), whereas the fourth optical sensing field 63' has a depth adapted to define the fourth scanning zone 64' for any selected value of first dimension (width).

In the example shown on FIGS. 8 and 9, for the sake of simplicity, the first and third scanning planes are substantially coplanar, whereas the second and fourth scanning planes are substantially coplanar. For so doing, the laser beams 55, 55' are conveniently oriented toward top and bottom surfaces 56, 56' respectively, in aligned and opposed directions. Similarly, the laser beams 65, 65' are oriented toward first and second side surfaces 66, 66', respectively, in aligned and opposed directions. However, it is to be understood that any other appropriate configuration of scanning planes may be employed.

According to the alternate configuration of the profile sensor units (not shown), the third sensing field 53' may be directed toward the travel path axis 13 within the third scanning plane (along Z axis of reference system 39), and similarly, the fourth sensing field 63' could be directed toward the travel path axis 13 within the fourth scanning plane. In that case, a similar compact arrangement may be obtained if the third laser beam 55' is crossing the central plane toward the third sensing field 53', whereas the fourth laser beam 65' is crossing the central plane toward the fourth sensing field 63'.

Figure 7:
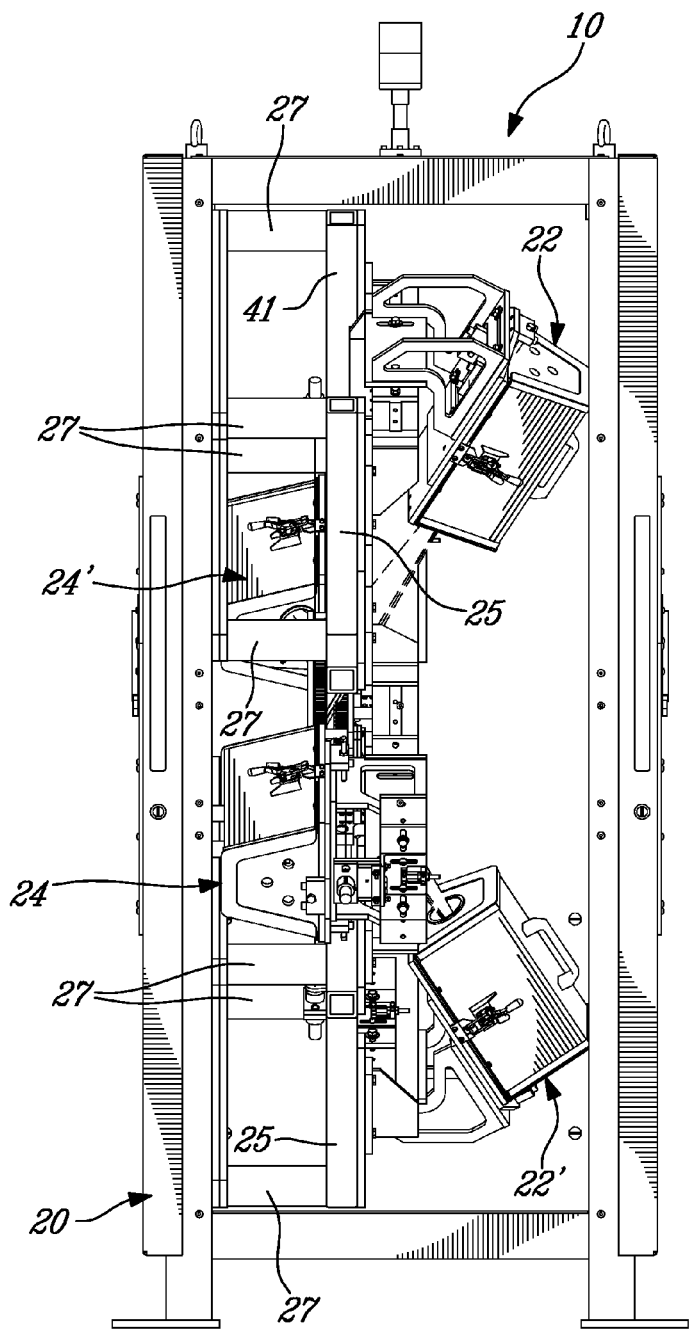
FIG. 7 is a side view of the apparatus of FIG. 1 with its enclosure wall and conveyer units not illustrated to better show the internal optical and mechanical components of the apparatus.

Various embodiments of an enclosure assembly for the cameras to be mounted on the frame of an optical inspection apparatus for scanning the profile of a surface of an article moving along a travel path axis will now be described with reference to FIGS. 10 to 13 in view of FIGS. 6 and 7 referred to above. The camera enclosure is used in the inspection apparatus to individually position, isolate and protect each camera from the board conveying path, particularly from board fragments that could be broken off during transport through the apparatus.

Figure 11:
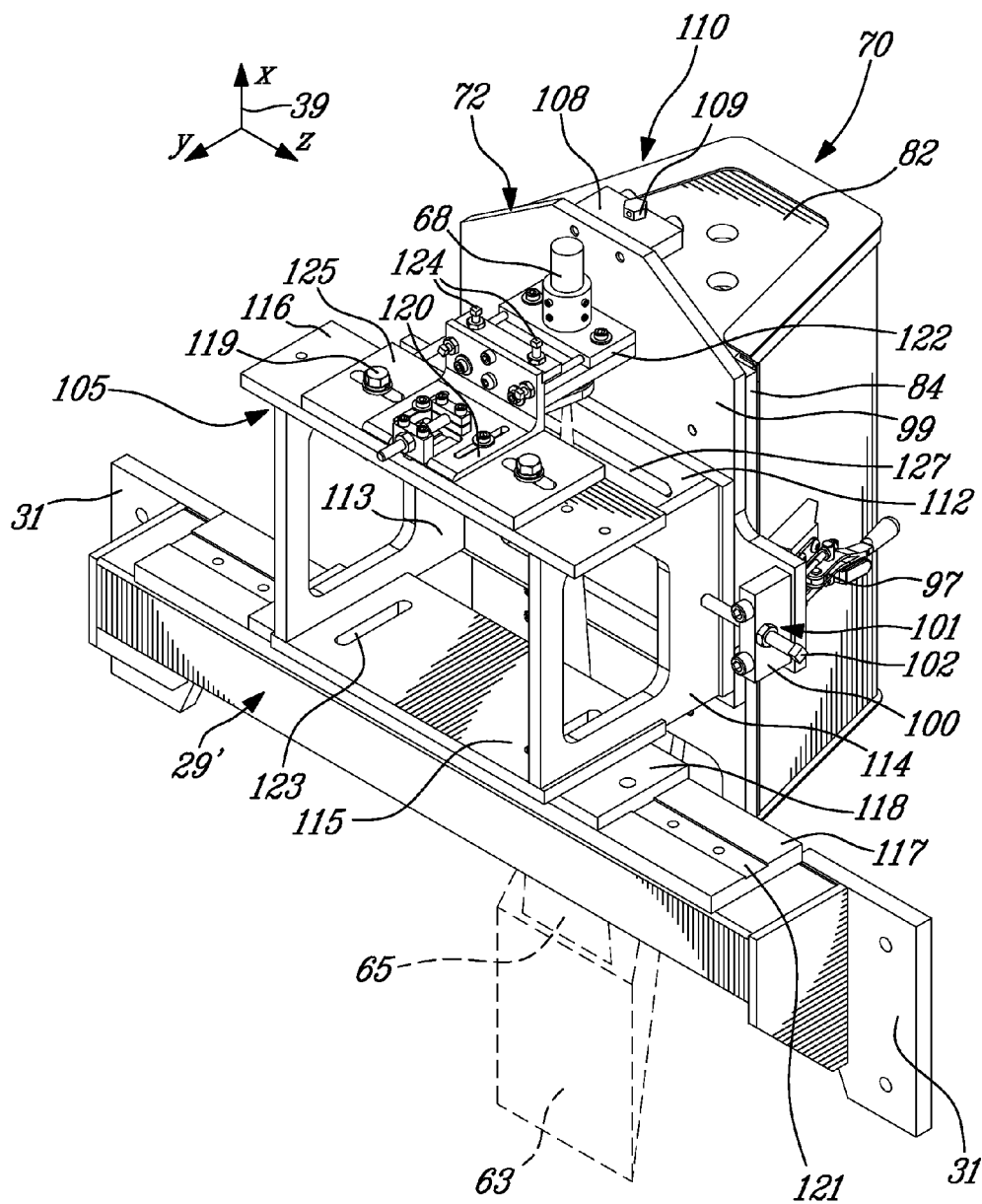
FIG. 11 is a perspective rear view of the profile sensor unit of FIG. 10.

Referring now to FIGS. 10 to 11, there is illustrated a profile sensor unit 24' (or 24) as provided on the inspection apparatus described above in view of FIGS. 6 to 9, showing a first design of camera enclosure assembly generally designated at 70, which includes an enclosure body 72 adapted to be secured to the apparatus frame through a mounting arrangement generally designated at 105, as better shown on FIG. 11. The mounting arrangement 105 has a back mounting plate 112 joined to lateral walls 113, 114 disposed in parallel spaced relationship and secured to a base mounting plate 115, over which walls a top plate 116 is secured. The base mounting plate 115 is provided with elongate apertures 123 for receiving bolts (not shown) providing position adjustment along axis Y on reference system 39, and is also adapted to be adjustably secured to a rail 117 using an intermediary plate 118 designed to fit onto a central groove 121 provided on the rail 117 for rough position adjustment along axis Z of reference system 39. The rail 117 is in turn attached to the support member 29' for the profile sensor unit 24' (or member 29 for unit 24), whose ends 31 are attached to the cross-bars 21, 21' secured to frame bars 23 through members 27 as described above with reference to FIG. 6 in view of FIG. 7. The top plate 116 is adapted to receive a mounting plate 125 having elongate openings for bolts 119, for adjustably securing a flanged element 120 mechanically coupled to a device 122 for securing the laser source 68 and orienting thereof according to the desired angular direction with respect to the optical sensing field 63, using set screws 124.

The camera enclosure assembly 70 has a front end wall 74 as shown on FIG. 10A provided with an opening 76 protected by an optical element 78 made of light transparent material such as glass or plastic. The enclosure body 72 further has a device 80 for mounting the camera 61 within the enclosure body such that it has its optical sensing field 63 directed toward opening 76. The front end wall 74 is arranged so that the optical element 78 extends in a plane perpendicular to the central direction of the optical sensing field 63 of camera 61, which is provided with a with a "Scheimpflug" adapter 62 in the example shown. The enclosure body 72 further has a rear end wall 82 and a base wall 84 provided with lateral guides 89, interposed between and joined to front and rear end walls 74, 82 so that all walls 74, 82, 84 form a peripheral edge 85 delimiting a space within which the camera is mounted. The front end wall 74 is secured and disposed with respect to base wall 84 using wedges 93 according to the preset triangulation angle of the camera 61 provided with "Scheimpflug" adapter 62, with reference to the corresponding plane of laser beam 65 which extends within the scanning plane in the example shown. The camera mounting device 80 has a back plate 88 on which is secured the camera surrounded by a cooling device 90, which back plate 88 is in turn secured to the base wall 84 through spacers 92. The camera mounting device 80 further has a lateral plate 86 for maintaining adjustment of the lens assembly 95 provided on the camera 61. Power supply, control and scanning output data lines to be linked to camera input/output block 81 as well as a cooling fluid line (not shown) can be introduced within enclosure body 72 through apertures 91 provided on rear end wall 82.

Turning to FIG. 10, the enclosure body 72 further includes an enclosure cover 94 having a closing edge 96 adapted to mate with the peripheral edge 85 to provide full closing of the camera mounting space, while allowing full access to this space when the cover 94 is brought to an open position. For so doing, the cover 94 has a handle 98 and the enclosure body 72 further includes a device 97 for releasably securing the enclosure cover 94 in its closed position, in the form of a latch in the example shown. It is to be understood that any other appropriate releasable securing device, clamp or fastener of a mechanical or magnetic type can also be used. In the example shown, the enclosure cover 94 is designed to be removable, the front and rear end walls 74, 82 having decreasing width from their junction with the base wall 84 toward corresponding portions of the peripheral edge 85 they form, to facilitate removal and closure of cover 94. It is to be understood that the cover 94 may alternately be designed to remain connected to the enclosure body using hinges when brought to its open position.

As shown on FIGS. 10 to 11, the base wall 84 is secured to an intermediate plate 99 provided on the enclosure assembly 70, a laterally protruding portion of which plate having a first flanged element 100 as part of a device 101 mechanically coupled to the enclosure body 72 for displacing thereof in a direction (along axis Z in reference system 39) perpendicular to the profile reference axis (axis X in reference system 39) and parallel to the scanning plane (corresponding to the plane of laser beam 65 in the example shown) to adjust the position of the optical sensing field with respect to the scanning plane. For so doing, the flanged element 100 receives a bolt 102 adapted to engage a corresponding threaded bore provided on the lateral wall 113 of the mounting arrangement 105, cooperating with guiding and securing bolts (not shown) engaging elongate apertures 127 provided on back mounting plate 112 as shown on FIG. 11, the device 101 allowing fine adjustment of the position of enclosure body 72 along axis Z in reference system 39 relative to the back mounting plate 112. It is to be understood that the adjustment device 101 may be provided on any other appropriate location with respect to the enclosure body, and that any other appropriate type of mechanical or electromechanical adjustment device can be used.

As also shown on FIGS. 10 to 11, the intermediate plate 99 provided on the enclosure assembly 70 has at rear end thereof a further protruding portion having a second flanged element 108 as part of a further device 110 mechanically coupled to the enclosure body 72 for displacing thereof in a direction parallel to the profile reference axis (axis X in reference system 39) to further adjust the position of the optical sensing field with respect to the scanning plane. For so doing, the flanged element 110 receives a bolt 109 adapted to engage a corresponding threaded bore provided on rear end wall 82. Cooperating with guiding and securing bolts 104 engaging elongate apertures 106 provided on base wall 84 as shown on FIG. 10A, the device 110 allows fine adjustment of position of the enclosure body 72 along axis X in reference system 39 relative to the intermediate plate 99. It is to be understood that the adjustment device 110 may be provided on any other appropriate location with respect to the enclosure body, and that any other appropriate type of mechanical or electromechanical adjustment device can be used.

Referring now to FIGS. 12 and 13, there is illustrated a profile sensor unit 22 (or 22') as provided on the inspection apparatus described above in view of FIGS. 6 to 9, showing a second design of camera enclosure assembly generally designated at 70', which includes an enclosure body 72' adapted to be secured to the apparatus frame through a mounting arrangement generally designated at 105', as better shown on FIG. 13. The mounting arrangement 105' has a back mounting plate 112' joined to lateral walls 113', 114' disposed in parallel spaced relationship and secured to a base mounting plate 115'. It can be seen that the lateral walls 113', 114' are designed so that the back mounting plate 112' and the base mounting plate 115' form one with another a preset angle which is related to the angle at which the laser source 58 directs with respect to the optical sensing field 53 the fan-shaped laser beam 55 toward the scanning zone. The base mounting plate 115' is provided with elongate apertures 123' for receiving bolts 126 providing position adjustment along axis Y on reference system 39, and is also adapted to be adjustably secured to a rail 117' using with an intermediary plate 118' designed to fit onto a central groove 121' provided on the rail 117' for rough position adjustment along axis X of reference system 39. The rail 117' is in turn attached to the support member 33 for the profile sensor unit 22 (or member 33' for unit 22'), whose ends 35 are attached to the cross-bars 25, 25' secured to frame bars 23 through members 27 as described above with reference to FIG. 6 in view of FIG. 7. Adjustably secured under support member 33 is a bottom plate 116' adapted to receive a mounting plate 125' having elongate openings for bolts (not shown), for adjustably securing a flanged element 120' mechanically coupled to a device 122' for securing the laser source 58 and orienting thereof according to the desired angular direction with respect to the optical sensing field 53, using set screws (not shown).

The other components of the enclosure assembly 70' are very similar to those described above with respect to enclosure assembly 70 in view of FIGS. 10 to 11. Amongst the variants, it can be seen from FIGS. 12 and 13 that the mounting device 80' as provided on enclosure body 72' has a lateral plate 86' designed for maintaining adjustment of a lens assembly 95 coupled to a camera 51 not provided with a "Scheimpflug" adapter, which camera 51 is nevertheless still mounted within the enclosure body 72' such that it has its optical sensing field 53 directed toward opening 76, with the front end wall 74 still arranged so that the optical element 78 extends in a plane perpendicular to the central direction of the optical sensing field 53. However, the lateral walls 113', 114' being designed according to a preset angle related to the angle at which the laser source 58 directs with respect to the optical sensing field 53 the fan-shaped laser beam 55 toward the scanning zone, the front end wall 74 is secured at right angle to the base wall 84 without the need of wedges in the example shown.

Furthermore, as shown on FIG. 13, the enclosure assembly 70', as compared with enclosure assembly 70 described above, is provided with a modified device 101' for displacing the enclosure body 72' in a direction (along axis X in reference system 39) perpendicular to the profile reference axis (axis Z in reference system 39) and parallel to the scanning plane (corresponding to the plane of laser beam 55 in the example shown) to adjust the position of the optical sensing field with respect to the scanning plane. As shown on FIG. 13 in view of FIG. 12, the base wall 84 is secured to an intermediate plate 99' provided on the enclosure assembly 70', a laterally protruding portion of which plate having a pair of flanged elements 100' as part of device 101', each of which receiving a bolt 102' adapted to engage a corresponding threaded bore provided on lateral wall 113', 114' of the mounting arrangement 105'. Cooperating with guiding and securing bolts 107 engaging elongate apertures 127' provided on back mounting plate 112' provided with a wide aperture 128 to lodge the device 101' as shown on FIG. 13, the device 101' allows fine adjustment of the position of enclosure body 72' along axis X in reference system 39 relative to the back mounting plate 112'. It is to be understood that the adjustment device 101' may be provided on any other appropriate location with respect to the enclosure body, and that any other appropriate type of mechanical or electromechanical adjustment device can be used.

Conveniently, a same device 110 as described above in view of FIGS. 10 to 11 is mechanically coupled to the enclosure body 72' for displacing thereof in a direction at angle with the profile reference axis (axis Z in reference system 39) to further adjust the position of the optical sensing field with respect to the scanning plane. Here again, it is to be understood that the adjustment device 110 may be provided on any other appropriate location with respect to the enclosure body, and that any other appropriate type of mechanical or electromechanical adjustment device can be used.

I claim:

1. An enclosure for an optical inspection apparatus for scanning the profile of at least one surface of an article moving along a travel path axis, the apparatus including a frame on which is mounted at least one profile sensor unit having a first optical sensing field directed toward said travel path axis and defining a first scanning zone associated with said surface as intersected by said sensing field, and a laser source directing at angle with said first sensing field a laser beam toward the scanning zone, to generate sensor output data related to the profile of said article surface, said enclosure comprising:

a peripheral portion connected to said frame and forming spaced apart peripheral edges defining a space in which said frame and said profile sensor unit are contained; and front end and rear end portions each having an opening aligned with said travel path axis to allow the movement of said article through the apparatus;

wherein at least one of said front and rear end portions is provided with a pair of access doors having outer closing edges adapted to mate with corresponding portions of the peripheral edges, and inner closing edges adapted to mate one with another at first portions thereof, wherein at least one of said inner closing edges is provided with a clearance at a second portion thereof to define a corresponding one of said openings whenever said access doors are brought one toward another to a closing position, said second portion is provided with at least one shielding element adjacent to said clearance to confine reflections of said laser beam within said enclosure while allowing the movement of said article.

2. An enclosure according to claim 1, wherein said shielding element is made of a flexible material.

3. An enclosure according to claim 1, wherein said inner closing edges are provided with respective clearances at second portions thereof cooperating to define said corresponding opening.

4. An enclosure according to claim 3, wherein each of said second portions is provided with said flexible shielding element.

5. An enclosure according to claim 1, wherein said access doors are sliding doors.

6. An enclosure according to claim 1, wherein said front and rear end portions are provided by respective pairs of said access doors whose respective said inner closing edges are provided with said clearance portions to define corresponding said openings whenever said access doors are brought one toward another to their respective closing positions.

* * * * *